United States Patent
Schatz et al.

(10) Patent No.: US 8,197,253 B2
(45) Date of Patent: Jun. 12, 2012

(54) MEDICAL OR DENTAL HANDPIECE HEAD

(75) Inventors: Norbert Schatz, Bürmoos (AT); Alois Gollackner, Thalgau (AT)

(73) Assignee: W&H Dentalwerk Bürmoos GmbH, Burmoos (AT)

( * ) Notice: Subject to any disclaimer, the term of this patent is extended or adjusted under 35 U.S.C. 154(b) by 0 days.

(21) Appl. No.: 11/545,980

(22) Filed: Oct. 10, 2006

(65) Prior Publication Data

US 2007/0087305 A1   Apr. 19, 2007

(30) Foreign Application Priority Data

Oct. 17, 2005   (EP) ..................................... 05022555

(51) Int. Cl.
*A61C 1/08* (2006.01)

(52) U.S. Cl. ....................................................... 433/126

(58) Field of Classification Search .......... 433/114–117, 433/125–128, 130–133; 215/216, 217, 237, 215/244; 604/164.01–164.09, 167.01–167.06, 604/168.01, 533–539; 606/4–6
See application file for complete search history.

(56) References Cited

U.S. PATENT DOCUMENTS

| | | | |
|---|---|---|---|
| 4,823,872 A * | 4/1989 | Hopmann | 166/217 |
| 5,254,004 A | 10/1993 | Feldman et al. | |
| 5,334,013 A * | 8/1994 | Meller | 433/132 |
| 5,699,922 A * | 12/1997 | Harding | 215/208 |
| 5,897,315 A * | 4/1999 | Nakayama et al. | 433/72 |
| 7,097,058 B2 * | 8/2006 | Wellman et al. | 215/330 |
| 2003/0209350 A1 * | 11/2003 | Laurel | 166/373 |

FOREIGN PATENT DOCUMENTS

| | | |
|---|---|---|
| AT | 404 551 | 12/1998 |
| JP | 08322852 | 12/1996 |
| JP | 2000087943 | 3/2000 |

OTHER PUBLICATIONS

English Translation of Naoki's reference (JP 2000087943).*
European Search Report for EP 05 02 2555, Mar. 13, 2006.

* cited by examiner

*Primary Examiner* — Sunl K Singh
(74) *Attorney, Agent, or Firm* — Klarquist Sparkman, LLP

(57) ABSTRACT

Described herein is a medical or dental handpiece head having a head sleeve detachably connected by a screw or threaded connection to a closing cap, and a locking device for locking the closing cap with the head sleeve. The locking device between the closing cap and the head sleeve is formed by at least one spring element. The locking device is designed and arranged so that unintentional release of the screw connection between the closing cap and the head sleeve caused by vibrations during operation of the handpiece can be suppressed.

21 Claims, 3 Drawing Sheets

MEDICAL OR DENTAL HANDPIECE HEAD

CROSS REFERENCE TO RELATED APPLICATION

The present application claims priority from pending European Patent Application No. 05022555.6, filed Oct. 17, 2005, which is incorporated herein by reference.

FIELD

The present invention relates to a medical handpiece head, in particular a dental handpiece head having a closing cap detachable from the handpiece head.

DESCRIPTION OF PRIOR ART

Such handpiece heads have long been known, see, for example, U.S. Pat. No. 5,254,004, wherein the closing cap is designed as a screw-on cover for a screw chuck, or Austrian patent AT 404,551, wherein a multipart closing cap is designed as a movable pressure cover by means of which the tool can also be released from the tool carrier.

The closing caps are detachably connected by a threaded connection to the handpiece head. The detachable feature is necessary to allow the components arranged in the interior of the handpiece head, e.g., the tool carrier, the bearings, the drive shafts, a rotor, etc. to be installed in the interior of the handpiece head during assembly. In addition, the detachable feature is also advantageous when maintenance is to be performed on components during use of the handpiece head or when worn components are to be replaced.

One disadvantage of the screw connection between the closing cap and the handpiece head is that there is the risk that the closing cap might become detached from the handpiece head due to vibrations generated or transmitted by the drive elements, in particular the rotor or one or more shafts, during operation of the handpiece head. This is the case in particular with handpiece heads with which the user on his own can replace components such as cartridges, including the tool carrier and the bearings, or can service elements. If the user then does not screw the closing cap on tightly enough, the risk of the cap becoming detached is especially great. Since components in the interior of the handpiece head are also mounted or supported on the closing cap, the result of the loosening of the closing cap may be that these components are released, displaced or detached, so that the handpiece head is no longer functional. If the closing cap becomes detached from the handpiece head during a treatment, in the worst case this may result in the tool that has been chucked in the tool carrier becoming detached in the patient's oral cavity.

SUMMARY

Described below are embodiments of a closing cap and a handpiece head that are detachably joined together by a threaded connection and in which the risk of unintentional detachment of the closing cap from the handpiece head is minimized.

The inventive handpiece head comprises a locking device or member between the closing cap and the handpiece head which is formed by at least one spring element, preferably one or more spring shackles or spring rings. The locking device or member locks the handpiece head, preferably the head sleeve, directly or indirectly to the closing cap, so that a frictionally engaged connection and/or a form-fitting connection is formed. Therefore, to release the screw connection between the handpiece head and the closing head, an additional force overcoming this locking is required. The vibrational forces occurring during use of the handpiece head are not sufficient to do so, so the locking device prevents the screw connection between the handpiece head and the closing cap from being released.

The locking device may be designed as part of the handpiece head or the locking cap or both elements. The locking device is preferably made of materials that can be sterilized, i.e., in particular materials which are designed so that they can withstand temperatures of at least one 120° C. , pressure fluctuations of approximately 3 bar or a chemically aggressive and corrosive environment for a period of at least approximately 10 minutes, depending on the type of sterilization. The locking device may be made of suitable heat-resistant plastics such as polyetheretherketone (PEEK) or polyphenyl sulfide (PPS) or metals, for example.

The use of these materials and in particular the use of metallic materials such as steel, nonferrous metals, aluminum or alloys containing these metals also has the advantage that the locking device has extremely little or no wear, e.g., due to shearing forces, even with repeated screwing and unscrewing of the thread joining the closing cap and the handpiece head. It is therefore not necessary to maintain or replace the locking device during the lifetime of the handpiece head. A locking device made of these materials is also essentially dimensionally stable, i.e., there is little or no change in its external shape even after prolonged use, and thus it retains its full chucking power and locking effect during the entire lifetime of the handpiece head.

The locking device is thus designed and arranged in the handpiece head in such a way that it prevents unwanted release of the closing cap from the handpiece head and/or from the head sleeve.

The foregoing other features and advantages will become more apparent from the following detailed description, which proceeds with reference to the accompanying figures.

DETAILED DESCRIPTION

Figure 1:
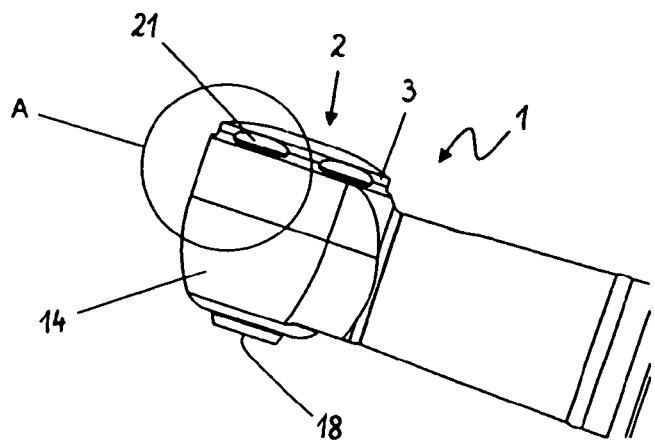
FIG. 1 shows a perspective diagram of an inventive handpiece head.

FIG. 1 shows a medical handpiece head, such as a dental handpiece head 1, and a closing cap 2 detachably connected to the handpiece head 1. The handpiece head 1, which can be detachably or undetachably connected to a handpiece, comprises an outer sleeve or head sleeve 14 surrounding an interior space 17 in which various components such as drive shafts, tool carriers, rotors operated with compressed air or other source of motive power, bearings for movably supporting of the tool carriers or the drive shafts, etc., are held in a known way. By means of an opening 18 in the head sleeve 14, a treatment instrument, e.g., a rotary drill or a file that can move back and forth can be inserted into the tool carrier. The handpiece head I illustrated in FIG. 1 is designed as an angled headpiece (contra-angle handpiece) in which the opening 18 and the tool carrier are arranged in such a way that a treatment instrument held therein protrudes at an angle away from the longitudinal axis of a handle section to be connected to the handpiece head 1.

The closing cap 2 consists of a cover section 3 which protrudes essentially beyond the handpiece head 1 when the closing cap 2 is connected to the angled headpiece 1 and consists of a connecting section 4 that is attached to the former and can be held in the interior 17 of the handpiece head 1. The connecting section 4 comprises one or more threads 5 which, together with the inside thread 6 of the head sleeve 14, forms a releasable screw connection by means of which the closing cap 2 is attached to the handpiece head 1 in a known way.

When connected to the handpiece head 1 in this way, the closing cap 2 fulfills several functions: it seals the interior 17 and prevents particles or treatment fluid from penetrating into the interior of the handpiece head 1. In particular, the connecting section 4 also serves to at least partially hold one or more of the components mentioned above and also to provide support for components. As an example, reference is made here to shoulder 19 which serves as an abutment for a ball bearing supporting the tool carrier in a rotating fashion. Finally, the closing cap 2 also plays a role in releasing a tool held in the tool carrier. If the tool carrier is designed as a screw chuck, then the closing cap 2 is designed as a screw cover having a bore 20 (see FIG. 4) through which can be inserted a tool for loosening the treatment instrument in the screw chuck. If the tool carrier is provided with a nonpositive or friction grip chuck, the closing cap 2 may be designed as a one-piece or multi-piece push cover that is held movably in the handpiece head 1 and has an engaging element that cooperates with the tool carrier in a known way, so that a treatment instrument chucked in the tool carrier can be extracted by the user.

At the outside of the closing cap 2, in the area of the cover section 3 there are provided one or more receptacles 21 in the form of recesses into which a tool can be inserted with the help of which the closing cap 2 can be unscrewed from the handpiece head 1. The components of the handpiece head 1 that are held in the interior space 17, in particular the bearings, shafts, the tool carrier or a cartridge comprising a compressed-air-operated rotor, the tool carrier and the ball bearings are therefore accessible for maintenance or for replacement.

To prevent unintentional release of the closing cap 2 from the handpiece head 1, a locking device, such as the locking device 7A, 7B or 7C is provided, designed as part of the closing cap 2 and/or the handpiece head 1. FIGS. 2, 3, 4 and 6 show advantageous exemplary embodiments of the locking device 7A, 7B and 7C. The part of the handpiece head 1 illustrated in these figures corresponds approximately to the detail labeled as "A" in FIG. 1.

Figure 2:
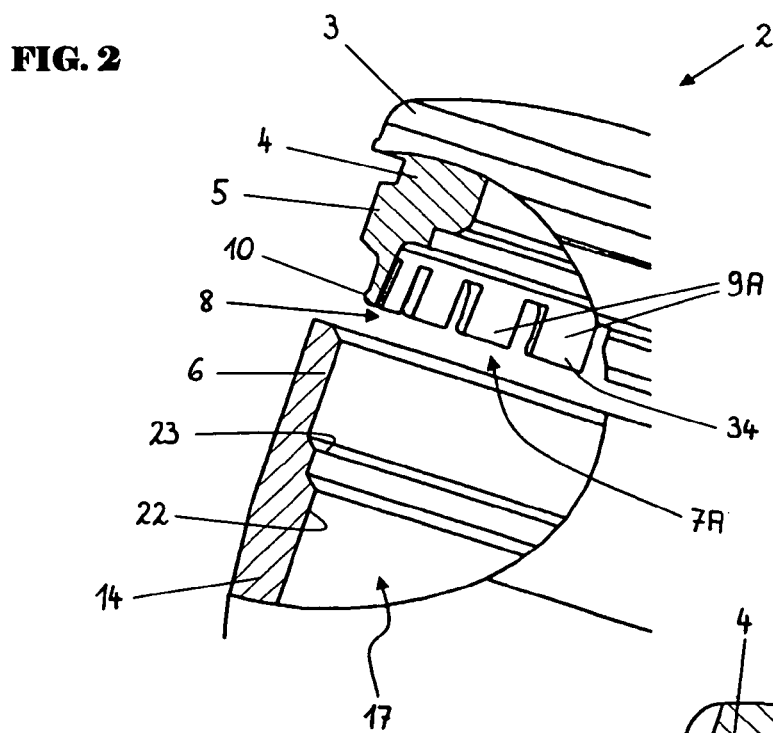
FIG. 2 shows a partial sectional diagram of a first exemplary embodiment of the inventive handpiece head and the inventive closing cap which has been separated from the handpiece head.

The locking device 7A with the spring element 8 in the form of multiple spring shackles 9A as illustrated in FIG. 2 is designed as part of the apron of connecting section 4 protruding away from the cover section 3 of the closing cap 2. Of course, only a single spring shackle 9A may also be provided. Each spring shackle 9A may execute a radial spring movement between a first released position as illustrated in FIG. 2 and a second tightened position (based on the longitudinal axis 11 of the handpiece head 1, see FIG. 4). When the closing cap 2 is screwed into the handpiece head 1, each spring shackle 9A travels along the inside 22 of the head sleeve 14 up to an area where the spring shackle 9A comes in contact with the inside 22 and is displaced by the inside 22 radially into the interior space 17 and thus into its second tightened position. This area may preferably be formed by a shoulder 23 protruding into the interior space 17.

Figure 3:
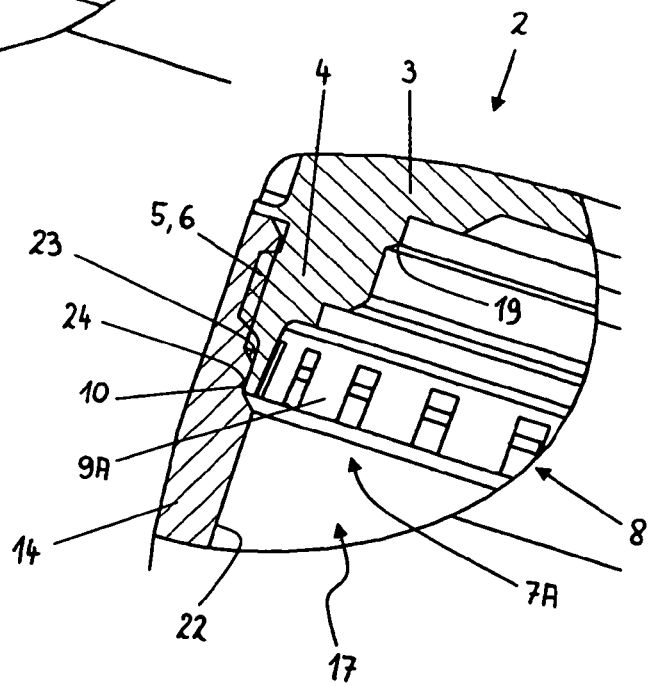
FIG. 3 shows a partial sectional diagram illustrating the handpiece head and the closing cap from FIG. 2, whereby the closing cap is connected to the handpiece head.

Due to the contact between the inside 22 of the head sleeve 14 and the spring shackles 9A in the second tightened position, there results a frictionally engaged connection (see FIG. 3). Therefore, to release the screw connection between the handpiece head 1 and the closing cap 2, an additional force is necessary to overcome the friction between the spring shackles 9A and the inside 22 of the head sleeve 14. The vibration forces occurring during use of the handpiece head 1 are not sufficient to accomplish this, so the frictionally engaged connection prevents the screw connection 5, 6 between the handpiece head 1 and the closing cap 2 from becoming loosened.

To improve the frictionally engaged connection, there is also the possibility of providing a nose 10 on one or more spring shackles 9A or roughening the surface of the spring shackle 9A and/or nose 10 coming in contact with the inside 22 or providing a friction-increasing coating. In addition, a recess 24 preferably in the form of a ring groove in which at least a portion of the spring shackle 9A and/or nose 10 engages may also be provided on the inside 22 of the handpiece head 1 so that the result is a combined frictionally engaged and form-fitting connection or even exclusively a form-fitting connection.

The advantage of the locking device 7A lies in particular in the simple and inexpensive method of production in which the spring shackles 9A are formed by cutting, in particular by milling or eroding them out of the connecting section 4. Since the entire closing cap 2, including the spring shackles 9A, consists of one part, no other assembly steps are necessary. Of course, a multi-piece construction can also be provided, if desired.

Figure 4:
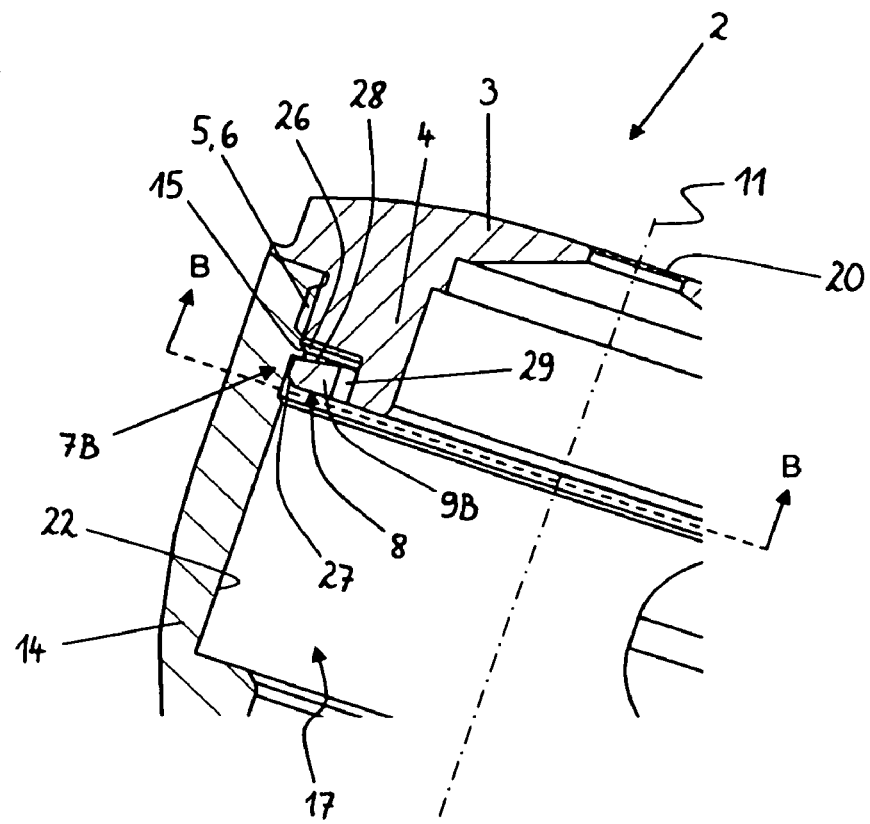
FIG. 4 shows a partial sectional diagram illustrating a second exemplary embodiment of the inventive handpiece head and the inventive closing cap.
Figure 5:
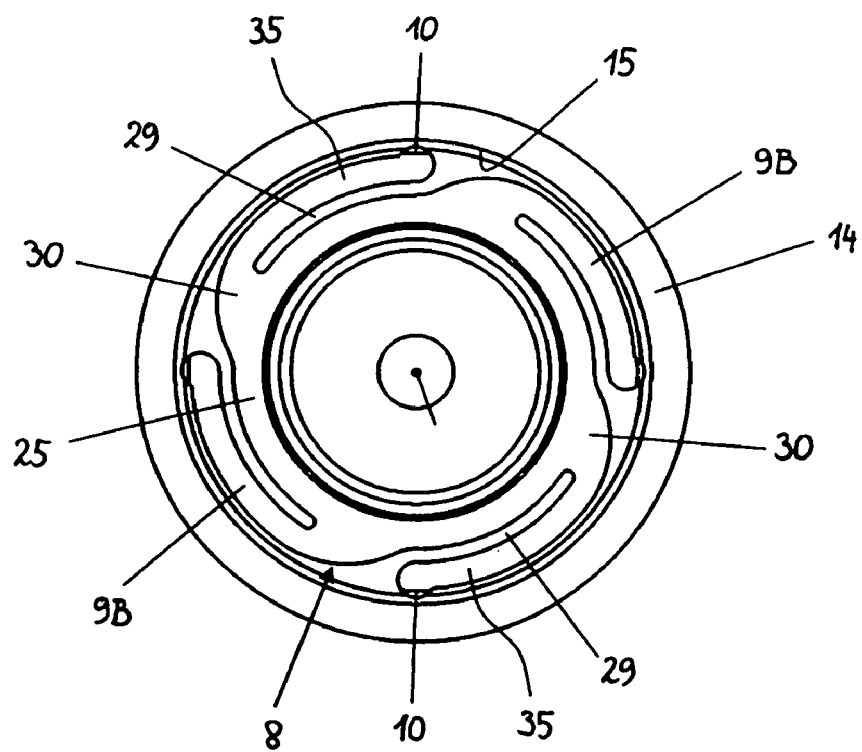
FIG. 5 shows a top view of the inventive handpiece head and the inventive closing cap along sectional plane B-B in FIG. 4.

FIGS. 4 and 5 illustrate an alternative embodiment of a locking device having shackles, whereby FIG. 5 shows a view of the head sleeve 14 and the closing cap 2 along the sectional plane B-B in FIG. 4. The locking device 7B comprises a spring element 8 having one or more spring shackles 9B, which are in turn preferably each provided with a nose 10. While the spring shackles 9A of FIGS. 2 and 3 run essentially parallel to the longitudinal axis 11 of the handpiece head 1, the spring shackles 9B extend in a generally circumferential direction and are arranged in a plane (running approximately parallel to the sectional plane B-B in FIG. 4) which runs essentially at a right angle to the longitudinal axis 11 of the handpiece head 1 (see FIG. 5 in particular).

The advantage of the locking device 7B is in particular the fact that less axial space is required for the spring shackles 9B. This is extremely important because the height (axial extent) of dental handpiece heads in particular should be as low as possible to allow the user good visibility of the treatment site in the patient's oral cavity while also permitting the least complicated handling of the handpiece head in difficultly accessible areas of oral cavity.

The spring shackles 9B are preferably designed as part of the closing cap 2 but alternatively they may also be manufactured with their base 25 as a separate component and connected to the closing cap 2, e.g., by pressing. Each spring shackle 9B is separated from the base 25 by a slot 29 and is connected to the base 25 via a web 30 so that each spring shackle 9B in turn can execute a radial spring movement between a first released position and a second tightened position. The functioning of the locking device 7B and the spring shackles 9B generally corresponds to the functioning described for the locking device 7A described above. Of course, the spring shackles 9B or the noses 10 may also be roughened to increase friction or provided with a friction-increasing coating.

FIG. 4 also shows that the inside 22 of the head sleeve 14 is provided with a wedge-shaped shoulder 15 which preferably runs in a ring along the entire inside 22. When screwing the handpiece head 1 together with the closing cap 2, the spring shackles 9B are displaced over the shoulder 15, whereby at the same time they also execute the radial movement until they engage behind shoulder 15, thus resulting in a reinforcement of the frictionally engaged connection and thus making it even more difficult to unintentionally loosen the closing cap 2 from the handpiece head 1. The shoulder 15 preferably has an inclined plane 26 on its side facing the closing cap and/or the spring shackles 9B each have a first inclined plane 27, so that displacement of the spring shackles 9B over the shoulder 15 when the handpiece head 1 is screwed onto the closing cap 2 is facilitated. In addition, each of the spring shackles 9B may have a second inclined plane 28 which is arranged on the side of the spring shackles 9B opposite the first inclined plane 27 and facilitates intentional loosening of the closing cap 2 from the handpiece head 1 by the user, for example.

Figure 6:
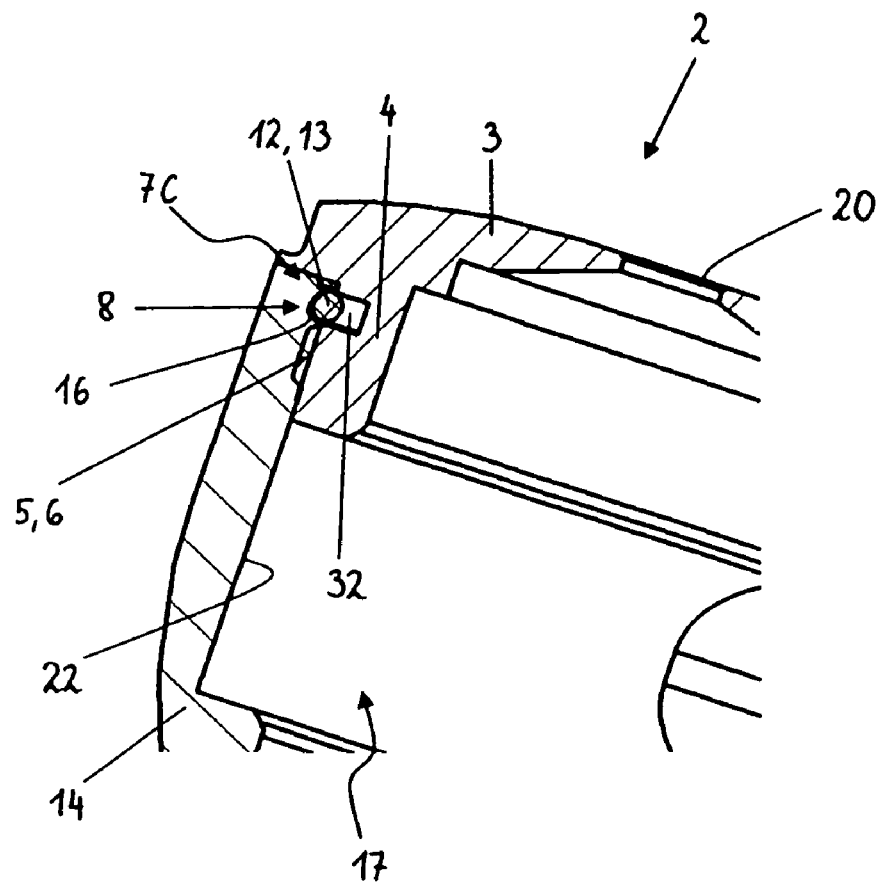
FIG. 6 shows a partial sectional diagram illustrating a third exemplary embodiment of the inventive handpiece head and the inventive closing cap.

FIG. 6 shows a locking device 7C whose spring element 8 comprises, instead of spring shackles, a spring ring 12 which is held at least partially in a recess 32 in the closing cap 2. The advantage of this embodiment lies first in the low axial height required by the spring ring 12 and secondly, the fact that manufacturing is further simplified by eliminating the step of forming the spring shackles.

The diameter of the spring ring 12 is such that the spring ring 12 comes in contact with the inside 22 of the head sleeve 14 when the closing cap 2 is screwed onto the handpiece head 1, thereby in turn establishing a frictionally locked connection.

A recess 16, e.g., a ring groove is preferably provided on the inside 22 of the head sleeve 14 so that the spring ring 12 engages in the recess 16 and the result is a combined frictionally locked and form-fitting connection or even exclusively a form-fitting connection.

Figure 7:
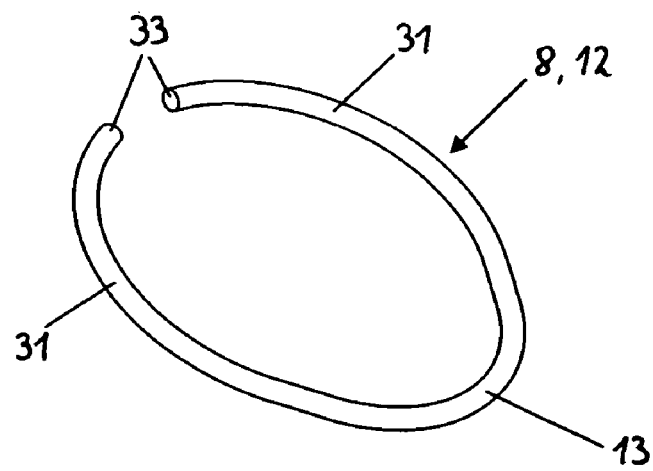
FIG. 7 shows the spring ring of the third exemplary embodiment according to FIG. 6.

The spring ring 12 may be designed as a circle, but, as shown in FIG. 7 in particular, it is preferably shaped in one location, so that spring ring 12 consists of a nose 13 having a first radius and two legs 31 having a second radius. Nose 13 protrudes further out of recess 32 than the two legs 31 when the handpiece head 1 and the closing cap 2 are screwed together, and it thus guarantees a secure and complete engagement in the recess 16. If nose 13 protrudes further than the depth of recess 32, the entire spring ring 12 is shifted or deformed during this screwing so that in particular, the two free ends 33 of the legs 31 protrude out of the recess 32 and into the recess 16, so that the spring 12 contacts the handpiece head 1 at several locations and reinforces the locking effect between the handpiece head 1 and the closing cap 2.

The spring elements 8 illustrated in FIGS. 2 through 7 have in common the fact that they have at least one free end 33, 34, 35. The at least one free end 33-35 is preferably put under tension in a first position and is movable between this first position and a second position so that the spring effect is executed by the free ends 33-35 and/or the locking effect is achieved directly or indirectly through the mobility. The mobility of the at least one free end 33-35 is greater here than the mobility of other parts of the locking device 7A, 7B, 7C, e.g., the base 25 or the web 30. Due to the prestress on the at least one free end 33-35, it is also advantageously not necessary to exert a force on the locking device 7A, 7B, 7C to achieve a locking effect. The pretension is selected so that the sum of all forces suppressing unintentional release of the closing cap 2 is greater than the forces occurring due to vibration during operation of the handpiece head 1 and causing the release of the closing cap 2 from the handpiece head 1.

The exemplary embodiments described here are not limiting, but instead include all possible embodiments that do not alter the basic functions and principles. In particular, it is possible to exchange parts of the locking device 7A, 7B or 7C between the handpiece head 1 and the closing cap 2 so that, for example, the spring element 8 may be arranged on the handpiece head 1 and the shoulder 15 or the recess 16 may be arranged on the closing cap 2.

In view of the many possible embodiments to which the disclosed principles may be applied, it should be recognized that the illustrated embodiments are only preferred examples and should not be taken as limiting in scope. Rather, the scope of protection is defined by the following claims. We therefore claim all that comes within the scope and spirit of these claims.

We claim:

1. A medical or dental handpiece head comprising:
a head sleeve and a closing cap, whereby the head sleeve and the closing cap can be repeatably and detachably joined together via a threaded screw connection, and
a locking device for locking the closing cap with the head sleeve, the handpiece head having a longitudinal axis extending in a direction that the closing cap moves while being screwed onto the head sleeve, wherein the locking device is formed by at least one spring element having at least one free end and the locking device is designed and arranged so that unintentional release of the screw connection between the closing cap and the head sleeve caused by vibrations during operation of the handpiece head can be suppressed, and wherein the at least one spring element is under pretension, while the cap is being screwed on the head sleeve, to spring in only a radial direction away from, and perpendicular to, the longitudinal axis so that it can be moved radially between a first released position and a second tightened position so that in the second tightened position, the spring element remains radially spaced apart from the closing cap to define a gap between the spring element and the closing cap and wherein the radial movement of the at least one spring element is achieved by screwing the closing cap on the head sleeve;
wherein the at least one spring element includes a nose having a first radius and opposing legs having a second radius, different than the first radius.

2. The handpiece head according to claim 1, wherein the at least one spring element is designed as a spring ring.

3. The handpiece head according to claim 2, wherein the spring ring is held at least partially in a recess.

4. The handpiece head according to claim 1, wherein the locking device additionally comprises at least one of a shoulder or a recess to hold at least one part of the at least one spring element, the at least one shoulder or recess being arranged radially to the locking element for radial engagement of the at least one spring element in the second tightened position.

5. The handpiece head according to claim 4, wherein the at least one spring element is designed as part of the closing cap.

6. The handpiece head according to claim 4, wherein the at least one spring element is designed as part of the head sleeve.

7. The handpiece head according to claim 1, wherein the handpiece head is for a dental handpiece.

8. The handpiece head according to claim 1, wherein the locking device comprises a heat resistant plastic.

9. The handpiece head according to claim 1, wherein the locking device comprises a metal.

10. The handpiece head according to claim 1, wherein when the closing cap is locked to the head sleeve by the locking device, an unlocking force exceeding a predetermined threshold is required to unlock the closing cap.

11. The handpiece head according to claim 4, wherein the shoulder or the recess is formed as part of the head sleeve.

12. The handpiece head according to claim 2 wherein the spring element comes in contact with the inside of the head sleeve and with the closing cap while the closing cap is screwed onto the handpiece head, thereby establishing a frictionally locked connection.

13. The handpiece head according to claim 1 wherein the at least one free end is put under tension in a first position and is movable between this first position and a second position so that the locking effect is executed by the free ends.

14. The handpiece head according to claim 1 wherein the mobility of the at least one free end is greater than the mobility of the other parts of the locking device.

15. A medical or dental handpiece head comprising:
a head sleeve and a closing cap, whereby the head sleeve and the closing cap can be repeatably and detachably joined together via a threaded screw connection, the handpiece having a longitudinal axis extending in a direction that the closing cap moves while being screwed onto the head sleeve, and
a locking device for locking the closing cap with the head sleeve, wherein the locking device is formed by at least one spring element having at least one free end and the locking device is designed and arranged so that unintentional release of the screw connection between the closing cap and the head sleeve caused by vibrations during operation of the handpiece head can be suppressed, and wherein the at least one spring element can be moved in a radial direction between a first released position and a second tightened position and wherein the locking device comprises a section at the inside of the head sleeve and a section at the closing cap which come in contact with the spring element while the closing cap is being screwed onto the handpiece head to create the radial movement in the spring element so as to spring in a direction only away from the longitudinal axis and before the second tightened position is reached, thereby establishing a frictionally locked connection and wherein the radial direction is perpendicular to a direction that the closing cap moves while being screwed onto the handpiece head;
wherein the at least one spring element sits within a recess and the at least one spring element includes a nose and at least one leg, wherein the nose protrudes further out of the recess than the at least one leg.

16. The handpiece head according to claim 15, wherein the locking device additionally comprises at least one of a shoulder or a recess to hold at least one part of the at least one spring element, the at least one shoulder or recess being arranged radially to the locking element for radial engagement of the at least one spring element in the second tightened position.

17. The handpiece head according to claim 4, wherein the handpiece head comprises a longitudinal axis and wherein the at least one shoulder or recess and the screw connection are arranged along the longitudinal axis.

18. The handpiece head according to claim 16, wherein the handpiece head comprises a longitudinal axis and wherein the at least one shoulder or recess and the screw connection are arranged in series with respect to the longitudinal axis.

19. The handpiece head according to claim 15, wherein the at least one spring element is connected to the closing cap such that the closing cap and the at least one spring element can be moved commonly along a longitudinal axis of the medical or dental handpiece head and relative to the head sleeve.

20. A medical or dental handpiece head comprising:
a head sleeve and a closing cap, whereby the head sleeve and the closing cap can be detachably and repeatably joined together via a threaded screw connection, and
a locking device for locking the closing cap with the head sleeve, wherein the locking device is formed by at least one spring element having at least one free end and the locking device is designed and arranged so that unintentional release of the screw connection between the closing cap and the head sleeve caused by vibrations during operation of the handpiece head can be suppressed, and wherein the at least one spring element can be moved radially between a first released position and a second tightened position and wherein the radial movement of the at least one spring element is achieved by screwing the closing cap on the head sleeve along a longitudinal axis and wherein the radial movement of the at least one spring element is only in a direction perpendicular to the longitudinal axis and wherein the at least one spring element is connected to the closing cap such that the closing cap and the at least one spring element can be moved commonly along a longitudinal axis of the medical or dental handpiece head and relative to the head sleeve;
wherein the at least one spring element sits within a recess and the at least one spring element includes a nose that protrudes further out of the recess than other portions of the at least one spring element.

21. The handpiece head according to claim 20, wherein the longitudinal axis is substantially perpendicular to the radial movement of the at least one spring element.

* * * * *

UNITED STATES PATENT AND TRADEMARK OFFICE
CERTIFICATE OF CORRECTION

| | | |
|---|---|---|
| PATENT NO. | : 8,197,253 B2 | Page 1 of 1 |
| APPLICATION NO. | : 11/545980 | |
| DATED | : June 12, 2012 | |
| INVENTOR(S) | : Schatz et al. | |

It is certified that error appears in the above-identified patent and that said Letters Patent is hereby corrected as shown below:

In the Specification

<u>Column 4</u>,
Lines 62-63, "in difficultly accessible areas" should be --in difficult to access areas--.

In the Claims

<u>Column 7</u>,
Line 31, "handpiece having a longitudinal" should be --handpiece head having a longitudinal--.

Signed and Sealed this
Twentieth Day of May, 2014

Michelle K. Lee
*Deputy Director of the United States Patent and Trademark Office*